United States Patent [19]

Eiermann et al.

[11] Patent Number: 6,011,182

[45] Date of Patent: Jan. 4, 2000

[54] PROCESS FOR PREPARING 2-CYCLOALKENONES

[75] Inventors: Matthias Eiermann, Limburgerhof; Klaus Ebel, Lampertheim; Jörg Botzem, Limburgerhof, all of Germany

[73] Assignee: BASF Aktiengesellschaft, Ludwigshafen, Germany

[21] Appl. No.: 09/241,300

[22] Filed: Feb. 1, 1999

[30] Foreign Application Priority Data

Feb. 12, 1998 [DE] Germany .................... 198 05 778

[51] Int. Cl.[7] ...................................... C07C 45/48
[52] U.S. Cl. .................. 568/338; 568/343; 568/347; 568/361
[58] Field of Search ..................... 568/338, 361, 568/343, 347

[56] References Cited

FOREIGN PATENT DOCUMENTS 008446  3/1980  European Pat. Off. .
2150294  10/1971  Germany .

OTHER PUBLICATIONS

*Polish J. Chem,* 71, pp. 149–169, 1997.

*Primary Examiner*—Gary Geist
*Assistant Examiner*—Sreeni Padmanabhan
*Attorney, Agent, or Firm*—Keil & Weinkauf

[57] ABSTRACT

The present invention relates to a process for preparing 2-cyclo-alkenones of the formula I

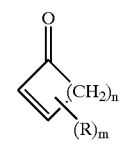

(I)

which comprises subjecting a 2-alkoxycycloalkanone and/or a 2-hydroxyalkanone ketal, in which n is an integer from 0 to 20, m is 0, 1, 2 or 3 and R is alkyl, alkylaryl, aryl, arylalkyl, alkenyl or alkynyl, to an elimination reaction in the gas phase on an acidic heterogeneous catalyst.

10 Claims, No Drawings

PROCESS FOR PREPARING 2-CYCLOALKENONES

The present invention relates to a process for preparing 2-cycloalkenones starting from 2-alkoxycycloalkanones or 2-hydroxycycloalkanone ketals by an elimination reaction in the gas phase on an acidic heterogeneous catalyst.

2-Cycloalkenones are starting materials or intermediates with many possible uses, inter alia for preparing pharmacologically active substances. Examples which may be mentioned are the preparation of carbazoles and carbazole derivatives as antiinflammatory agents with relevance in veterinary medicine as disclosed in EP-A-008 446, and the preparation of prostaglandins starting from 2-cyclopentenones.

Nevertheless, the known processes for the industrial preparation of 2-cycloalkenones have considerable disadvantages. Known processes based on precursors which can be obtained easily and cheaply in industrial quantities are industrially complicated or result in byproducts which are difficult to utilize. Examples thereof are the Birch reduction of anisole, a complicated multistage process which uses sodium and liquid ammonia, provides only moderate yields and, moreover, is confined to the preparation of 2-cyclohexenone, and the oxidation of cycloalkenes with peroxides (J. Mlochowski, S. B. Said, Polish J. Chem. 1997, 71, p. 149) which, because of low selectivity, results in a large number of byproducts which are difficult to remove.

An industrial process is disclosed in DE-A-21 50 294. This entails thermal elimination of hydrogen halide from 2-halocyclohexanone or the relevant carboxylic acid from 2-acyloxycyclohexanone. The serious disadvantages of this process will be indicated taking the example of the preparation of 2-cyclohexenone from 2-chlorocyclohexanone. In this case, the cyclohexanone must be first ketalized, then chlorinated, dehydrochlorinated and subsequently subjected to an acidic ketal cleavage. In addition, the chlorination results in regioisomers and polychlorination products, which must be removed or may result in the formation of mixtures of 2- and 3-cyclohexenone products which in turn require complicated separation or isomerization.

It is an object of the present invention to provide a widely applicable process for preparing 2-cycloalkenones which is based on precursors which can easily be obtained in industrial quantities and affords the required cycloalkenones in the minimum number of stages.

We have found that this object is achieved by preparing the required 2-cycloalkenones in a simple manner, in one stage and in good yields by elimination, with acidic heterogeneous catalysis, from the easily obtainable 2-alkoxycycloalkanones or 2-hydroxycycloalkanone ketals.

The present invention therefore relates to a process for preparing 2-cycloalkenones of the formula I

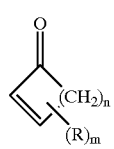

(I)

which comprises subjecting a 2-alkoxycycloalkanone of the formula II

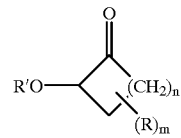

(II)

or a 2-hydroxycycloalkanone ketal of the formula III

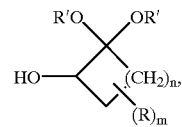

(III)

where
n is an integer from 0 to 20, preferably 1 to 8, particularly preferably 2 and 3,
m is 0, 1, 2 or 3,
the R radicals are, independently of one another, alkyl, alkylaryl, aryl, arylalkyl, alkenyl or alkynyl, it being possible for the aryl radicals to have one or two substituents which are selected, independently of one another, from alkyl, hydroxyl or alkoxy,
the R' radicals are, independently of one another, alkyl or alkenyl or, in formula III, may together be $C_1$–$C_5$-alkylene or $C_2$–$C_5$-alkenylene,
or a mixture of the compounds of the formulae II and III to an elimination reaction in the gas phase on an acidic heterogeneous catalyst.

Alkyl (also in alkylaryl, alkoxy etc.) comprises straight-chain or branched alkyl groups which preferably have 1 to 12, in particular 1 to 6, carbon atoms. Examples are methyl, ethyl, n-propyl, isopropyl, n-butyl, sec-butyl, isobutyl, t-butyl, n-hexyl, 2-ethylhexyl and n-dodecyl.

Aryl is, in particular, phenyl or naphthyl.

Alkenyl comprises straight-chain or branched alkenyl groups preferably having 2 to 6 carbon atoms. Examples are allyl, methallyl, 2-butenyl and 3-butenyl.

Alkynyl comprises straight-chain or branched alkynyl groups preferably having 2 to 6 carbon atoms. Examples are 2-propynyl, 2-butynyl and 3-butynyl.

The preferred meanings in the above formulae are:
R is H (m=0), alkyl or aryl, which is unsubstituted or substituted by one or two alkyl, hydroxyl or alkoxy radicals. R is particularly preferably H;
m is 0 or 1;
n is 2 to 5, in particular 2 to 4; and
R' is alkyl or $C_1$–$C_5$-alkylene.

It is particularly preferred to prepare 2-cyclopentenone and 2-cyclohexenone respectively from 2-hydroxycyclopentanone $C_1$–$C_6$-dialkyl ketal and 2-hydroxycyclohexanone $C_1$–$C_6$-dialkyl ketal or $C_1$–$C_6$-alkoxycyclopentanone and $C_1$–$C_6$-alkoxycyclohexanone.

It is preferred according to the invention to use an acidic heterogeneous catalyst which comprises at least one oxide or phosphate, or a mixture of oxides and phosphates, or mixed oxides of elements of groups 3 to 6 and 13 to 15 of the Periodic Table, numbered according to their current IUPAC recommendation. The acidic heterogeneous catalyst comprises in particular oxides of titanium, zirconium, aluminum, silicon, and/or phosphates of zirconium, lanthanum and cerium, particularly preferably $TiO_2$, $ZrO_2$, $Al_2O_3$, $SiO2$ and $LaPO_4$.

The acidic heterogeneous catalyst is preferably additionally impregnated with one or more acidic compounds. Suitable acidic compounds comprise mineral acids such as phosphoric acid, nitric acid, sulfuric acid, hydrochloric acid, their condensed forms such as pyrophosphoric acid, pyrosulfuric acid, and their metal or ammonium salts. By metals are meant the elements of groups 1 to 14 of the Periodic Table, numbered according to the current IUPAC recommendation, but especially the alkali metals and alkaline earth metals. The term ammonium stands for the protonated or alkylated form of ammonia or of a mono-, di- or trialkylamine, it being possible for the alkyl radicals independently of one another to have 1 to 20, in particular 1 to 6, carbon atoms. The acidic heterogeneous catalyst may, where appropriate, be applied to a carrier. Suitable carriers are silicon dioxide (silica gel), aluminum oxide, silicon carbide, silicon nitride, graphite, zeolites and other solids which are inert under the reaction conditions.

The amount of acidic compound is generally in the range from 1 to 70% by weight, preferably 5 to 50% by weight, based on the oxide or phosphate.

The novel process is generally carried out continuously, in particular in a tubular reactor. The catalyst is moreover generally used in particulate form, e.g. in the form of extrudates, tablets or beads. Use as a fixed bed is preferred.

The acidic heterogeneous catalysts used according to the invention are also subject to the usual gradual deactivation on use in gas-phase reactions, but they can advantageously be completely regenerated thermally in the reactor in the presence of atmospheric oxygen, preferably at temperatures above 300° C., particularly preferably at temperatures above 400° C., so that regular operation of the reactor is ensured without time-consuming and costly replacement of the catalyst.

It is possible in the novel process for the starting materials to be passed without solvent or together with the vapor of a solvent over the acidic heterogeneous catalyst. Examples of suitable solvents are water, alcohols, such as methanol, ethanol, isopropanol etc., ethers such as tetrahydrofuran, ethylene glycol monomethyl ether, ethylene glycol dimethyl ether etc., and dimethylformamide and N-methylpyrrolidinone. The novel process is preferably carried out without the addition of solvents or in the presence of water.

The novel process can be carried out in a wide range of temperatures and pressures. The skilled worker will choose them so that all the reactants and products and the solvent which is employed where appropriate are present in vapor form, and an adequate space-time yield is achieved. The novel elimination reaction is preferably carried out at a temperature in the range from 200 to 500° C., particularly preferably in the range from 300 to 450° C. The preferred pressures are in the range from 10 mbar to 5 bar, and it is particularly preferably carried out under atmospheric pressure.

It is possible to prepare the 2-alkoxycycloalkanones (II) and 2-hydroxycycloalkanone ketals (III) required for this process in a variety of ways, for example by ketalization of the appropriate hydroxycycloalkanone derived, where appropriate, from an acyloin condensation (X. Creary, A. J. Rollin, J. Org. Chem. 1977, 42, 4231).

An important advantage of the novel process is, however, that starting materials of the formulae II and III can easily be prepared in industrial quantities by an electrochemical reaction between the appropriate cycloalkanone and the appropriate alcohols. One process for this is disclosed in EP-A-460 451, which is incorporated herein by reference.

The product obtained according to the invention may, if desired, be purified in a usual manner, e.g. by distillation. It is advisable to use fractional distillation. Depending on the boiling point of the product vacuum distillation is used. Generally, distillation is carried out at a pressure in the range of about 10 mbar to 1 bar.

It has been found to be advantageous to separate off the water contained in the feed material during distillation by adding a suitable azeotrope forming agent, e.g. toluene.

Prior to distillation possibly present acid traces may be neutralized with bases such as alkali hydroxides, alkali carbonates or alkali bicarbonates, e.g. sodium or potassium hydroxide, carbonate or bicarbonate.

The following examples are intended to illustrate the novel process without, however, restricting the scope of the invention.

EXAMPLES

Example 1

Silicon dioxide impregnated with 20% by weight phosphoric acid was used as catalyst. The catalyst was in the form of 4 mm pellets. 0.1 mol/h nitrogen and 15 ml/h liquid 2-hydroxycyclohexanone dimethyl ketal were metered from above into a electrically heated silica glass tubular reactor which was arranged vertically and which contained at the bottom 10 ml of silica rings, then the catalyst (27.5 g) as pellets and subsequently a further 20 ml of silica rings, at an internal temperature of 350° C. The top layer of silica rings acted as vaporizer and caused negligible chemical reaction of the starting material. The gases emerging at the lower end were fed to a condenser operated with cooling water. The conversion of the 2-hydroxycyclohexanone dimethyl ketal was>99%. The condensate contained 2-cyclohexenone in a yield of about 63% of theory. The 2-cyclohexenone was obtained with a purity>99% after distillation.

Example 2

The process was carried out as in Example 1 but using in place of pure 2-hydroxycyclohexanone dimethyl ketal a 1:1 mixture thereof with 2-methoxycyclohexanone as starting material. The condensate contained 64% 2-cyclohexenone.

We claim:

1. A process for preparing 2-cycloalkenones of the formula I

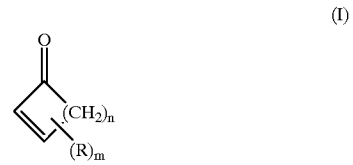

(I)

which comprises subjecting a 2-alkoxycycloalkanone of the formula II

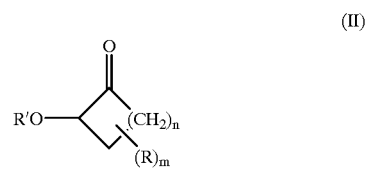

(II)

or a 2-hydroxycycloalkanone ketal of the formula III

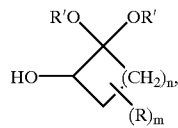

(III)

in which
- n is an integer from 0 to 20,
- m is 0, 1, 2 or 3,
- R is alkyl, alkylaryl, aryl, arylalkyl, alkenyl or alkynyl, it being possible for the aryl radicals to have one or two substituents which are selected, independently of one another, from alkyl, hydroxyl or alkoxy,
- the R' radicals are, independently of one another, alkyl or alkenyl or, in formula III, may together be $C_1$–$C_5$-alkylene or $C_2$–$C_5$-alkenylene, or a mixture of the compounds of the formulae II and III to an elimination reaction in the gas phase on an acidic heterogeneous catalyst, whichgeneous catalyseneous catalyst comprises
  (i) at least one oxide or a mixed oxide of elements of groups 3 to 6 and 13 to 15 of the Periodic Table and is impregnated with one or more mineral acids or metal or ammonium salts of the mineral acids; or
  (ii) at least one phosphate or a mixture of oxides and phosphates of elements of groups 3 to 6 and 13 to 15 of the Periodic Table and, optionally, is additionally impregnated with one or more mineral acids or metal or ammonium salts of the mineral acids; or
  (iii) a mixture of (i) and (ii).

2. A process as claimed in claim 1, wherein $SiO_2$, $TiO_2$, $ZrO_2$, or $Al_2O_3$ which is impregnated with a mineral acid or an ammonium salt of the mineral acid, is used as acidic heterogeneous catalyst.

3. A process as claimed in claim 1, wherein the starting materials are passed without solvent or together with the vapor of a solvent over the acidic heterogeneous catalyst.

4. A process as claimed in claim 1, wherein the elimination reaction is carried out in the range from 200° C. to 500° C.

5. A process as claimed in claim 1, wherein the elimination reaction is carried out under pressures in the range from 10 mbar to 5 bar.

6. A process as claimed in claim 1, wherein the compounds of the formulae II and III are prepared by an electrochemical reaction between a cycloalkanone and an alcohol.

7. A process as claimed in claim 1, wherein the product of the process is neutralized by adding a base.

8. A process as claimed in claim 1, wherein the product of the process is purified by distillation.

9. A process as claimed in claim 8, wherein the water present is separated off during distillation.

10. A process as claimed in claim 1, wherein $LaPO_4$, which is optionally impregnated with a mineral acid or an ammonium salt, is used as acidic heterogeneous catalyst.

* * * * *

UNITED STATES PATENT AND TRADEMARK OFFICE
CERTIFICATE OF CORRECTION

PATENT NO.: 6,011,182

DATED: January 4, 2000

INVENTOR(S): EIERMANN et al.

It is certified that error appears in the above-identified patent and that said Letters Patent is hereby corrected as shown below:

Col. 5, claim 1, line 22, delete "whichgeneous catalyseneous catalyst comprises" and substitute --which acidic heterogeneous catalyst comprises--.

Signed and Sealed this

First Day of August, 2000

*Attest:*

Q. TODD DICKINSON

*Attesting Officer*          *Director of Patents and Trademarks*